(12) United States Patent
Song et al.

(10) Patent No.: US 10,934,320 B2
(45) Date of Patent: Mar. 2, 2021

(54) CARBENE PRECURSOR COMPOUND AND USE THEREOF

(71) Applicants: INSTITUTE FOR BASIC SCIENCE, Daejeon (KR); POSTECH ACADEMY-INDUSTRY FOUNDATION, Pohang-si (KR)

(72) Inventors: Hayoung Song, Seoul (KR); Kimoon Kim, Pohang-si (KR); Eunsung Lee, Pohang-si (KR); Hyunho Kim, Pohang-si (KR)

(73) Assignees: INSTITUTE FOR BASIC SCIENCE, Daejeon (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 16/352,562

(22) Filed: Mar. 13, 2019

(65) Prior Publication Data

US 2019/0284218 A1    Sep. 19, 2019

(30) Foreign Application Priority Data

Mar. 13, 2018 (KR) .................. 10-2018-0029072

(51) Int. Cl.
| | | |
|---|---|---|
| *C07F 15/00* | (2006.01) | |
| *B01J 31/22* | (2006.01) | |
| *H01L 51/00* | (2006.01) | |
| *C07D 265/18* | (2006.01) | |
| *H01L 51/50* | (2006.01) | |

(52) U.S. Cl.
CPC ....... *C07F 15/0073* (2013.01); *B01J 31/2295* (2013.01); *C07D 265/18* (2013.01); *H01L 51/0084* (2013.01); *H01L 51/5004* (2013.01); *H01L 51/5012* (2013.01); *H01L 2251/552* (2013.01)

(58) Field of Classification Search
CPC .................................................. C07F 15/0073
See application file for complete search history.

(56) References Cited

PUBLICATIONS

Hayoung Song et al., Synthesis of Coumaraz-2-on-4-ylidene, 19th IUPAC International Symposium on Organometallic Chemistry Directed Towards Organic Synthesis (OMCOS19), Jun. 25-29, 2017, IUPAC, Jeju, Republic of Korea.
Hayoung Song et al., Synthesis of Coumaraz 2-on-4-ylidene, 6th Asian Conference on Coordination Chemistry (ACCC6), Jul. 23-28, 2017, ACCC, Victoria, Australia.
Hayoung Song et al., Synthesis of Coumaraz 2-on-4-ylidene: The most π-acidic N-heterocyclic Carbene, 120th General Meeting of Korean Chemical Society, Oct. 18-20, 2017, KCS, Gwangju, Republic of Korea.
Hayoung Song et al., Synthesis of Coumaraz 2-on-4-ylidene, 2017 Summer Inorganic Chemistry Symposium, Jul. 21-22, 2017, 2017 Inorganic Chemistry division of KCS, Gyeongju, Republic of Korea.
Hayoung Song et al., Activation of Small Molecules at N-Heterocyclic Carbene Centers, Synlett 2016, Nov. 11, 2015, p. 477-485, vol. 27(04), Georg Thieme Verlag Stuttgart, New York, U.S.

*Primary Examiner* — Bruck Kifle
(74) *Attorney, Agent, or Firm* — Hauptman Ham, LLP

(57) ABSTRACT

Provided are a transition metal compound including a novel carbene compound as a ligand, a preparation method thereof, and an application thereof. The transition metal compound according to the present invention may form a structurally stable complex and also have a HOMO-LUMO energy gap and singlet-triplet transition energy which are significantly low as compared with a conventional transition metal compound. In addition, according to the present invention, the transition metal compound may be synthesized in large quantities by a very simple method, thereby having high commercial utility, and thus, an application using the compound is expected.

10 Claims, No Drawings

CARBENE PRECURSOR COMPOUND AND USE THEREOF

CROSS-REFERENCE TO RELATED APPLICATIONS

This application claims priority under 35 U.S.C. § 119 to Korean Patent Application No. 10-2018-0029072, filed on Mar. 13, 2018, in the Korean Intellectual Property Office, the disclosure of which is incorporated herein by reference in its entirety.

TECHNICAL FIELD

The following disclosure relates to a novel carbene precursor compound and a use thereof.

BACKGROUND

Recently, an N-heterocyclic carbene (NHC) compound has appeared as a novel family of a ligand for developing a homogeneous catalyst.

The N-heterocyclic carbene compound has received attention as a ligand capable of effectively stabilizing an unstable transition metal compound abundant in electrons, and a study of activation of various chemical bonds based on high reactivity has been attempted (Non-Patent Document 1).

According to the study, it is suggested that the reactivity of the N-heterocyclic carbene compound is strongly influenced by a highest occupied molecular orbital-lowest unoccupied molecular orbital (HOMO-LUMO) energy gap and singlet-triplet transition energy.

Thus, the present inventors extensively studied the N-heterocyclic carbene compound having a low HOMO-LUMO energy gap, and as a result, devised a coumaraz-2-on-4-ylidene-based compound which is an N-heterocyclic carbene compound having a new structure, and found that development of a new synthesis method of a carbene precursor compound for the coumaraz-2-on-4-ylidene-based compound and a ligand derived therefrom may greatly change electrical/chemical stereostructure of a transition metal compound, thereby completing the present invention.

RELATED ART DOCUMENTS

Patent Documents (Non-Patent Document 1) Synlett 2016; 27(04), 477-485

SUMMARY

An embodiment of the present invention is directed to providing a transition metal compound having a novel structure including a ligand derived from an N-heterocyclic carbene compound and a preparation method thereof.

Another embodiment of the present invention is directed to providing a use of the transition metal compound.

Another embodiment of the present invention is directed to providing a new N-heterocyclic carbene compound having a low HOMO-LUMO energy gap and low singlet-triplet transition energy as compared with a conventional carbene compound.

In one general aspect, a transition metal compound represented by the following Chemical Formula 1 is provided:

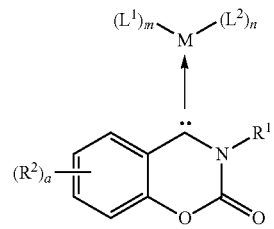

[Chemical Formula 1]

wherein

M is a transition metal;

m is an integer of 1 or 2, n is an integer of 0 to 2, and m+n+1 is an oxidation number of a used transition metal;

$L^1$ is a halogen;

$L^2$ is a monodentate ligand or a bidentate ligand;

a is an integer of 0 to 4;

$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocycloalkyl, $C_6$-$C_{30}$ aryl, and $C_6$-$C_{30}$ heteroaryl;

$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocycloalkyl, $C_6$-$C_{30}$ aryl, and $C_6$-$C_{30}$ heteroaryl, and when a is an integer of 2 or more, $R^1$ may be the same or different; and alkyl, alkenyl, alkynyl, cycloalkyl, heterocycloalkyl, aryl, or heteroaryl of $R^1$ and alkyl, alkenyl, alkynyl, alkoxy, alkenyloxy, alkynyloxy, alkylamino, cycloalkyl, heterocycloalkyl, aryl, or heteroaryl of $R^2$ may be independently of one another further substituted by one or more substituents selected from the group consisting of halogen, hydroxy, cyano, $C_1$-$C_{30}$ alkyl, and halo$C_1$-$C_{30}$ alkyl, and heterocycloalkyl or heteroaryl of $R^1$ and $R^2$ independently of each other contains one or more selected from the group consisting of B, N, O, S, Se, —P(=O)—, —C(=O)—, Si, and P.

In another general aspect, a preparation method of the transition metal compound is provided.

A preparation method of the transition metal compound may include: a step of reacting a compound of the following Chemical Formula A with a carbonate precursor to prepare a compound of the following Chemical Formula B, and reacting a transition metal precursor in the presence of an organic base:

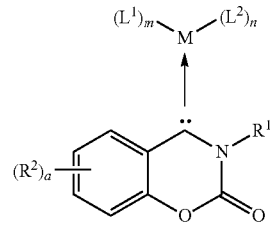

[Chemical Formula 1]

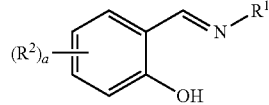

[Chemical Formula A]

-continued

[Chemical Formula B]

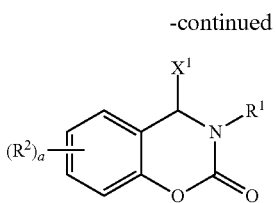

wherein

M is a transition metal;

m is an integer of 1 or 2, n is an integer of 0 to 2, and m+n+1 is an oxidation number of a used transition metal;

$L^1$ is a halogen;

$L^2$ is a monodentate ligand or a bidentate ligand;

$X^1$ is a halogen;

a is an integer of 0 to 4;

$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocycloalkyl, $C_6$-$C_{30}$ aryl, and $C_6$-$C_{30}$ heteroaryl;

$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocycloalkyl, $C_6$-$C_{30}$ aryl, and $C_6$-$C_{30}$ heteroaryl, and when a is an integer of 2 or more, $R^1$ may be the same or different; and alkyl, alkenyl, alkynyl, cycloalkyl, heterocycloalkyl, aryl, or heteroaryl of $R^1$ and alkyl, alkenyl, alkynyl, alkoxy, alkenyloxy, alkynyloxy, alkylamino, cycloalkyl, heterocycloalkyl, aryl, or heteroaryl of $R^2$ may be independently of one another further substituted by one or more substituents selected from the group consisting of halogen, hydroxy, cyano, $C_1$-$C_{30}$ alkyl, and halo$C_1$-$C_{30}$ alkyl, and heterocycloalkyl or heteroaryl of $R^1$ and $R^2$ independently of each other contains one or more selected from the group consisting of B, N, O, S, Se, —P(=O)—, —C(=O)—, Si, and P.

In another general aspect, a catalyst composition includes the transition metal compound.

In another general aspect, an organic electroluminescent element includes the transition metal compound.

In still another general aspect, a carbene compound represented by the following Chemical Formula 2, that is, an N-heterocyclic carbene compound is provided:

[Chemical Formula 2]

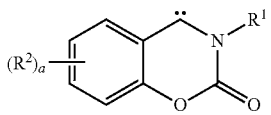

wherein a is an integer of 0 to 4;

$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocycloalkyl, $C_6$-$C_{30}$ aryl, and $C_6$-$C_{30}$ heteroaryl;

$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocycloalkyl, $C_6$-$C_{30}$ aryl, and $C_6$-$C_{30}$ heteroaryl, and when a is an integer of 2 or more, $R^1$ may be the same or different; and alkyl, alkenyl, alkynyl, cycloalkyl, heterocycloalkyl, aryl, or heteroaryl of $R^1$ and alkyl, alkenyl, alkynyl, alkoxy, alkenyloxy, alkynyloxy, alkylamino, cycloalkyl, heterocycloalkyl, aryl, or heteroaryl of $R^2$ may be independently of one another further substituted by one or more substituents selected from the group consisting of halogen, hydroxy, cyano, $C_1$-$C_{30}$ alkyl, and halo$C_1$-$C_{30}$ alkyl, and heterocycloalkyl or heteroaryl of $R^1$ and $R^2$ independently of each other contains one or more selected from the group consisting of B, N, O, S, Se, —P(=O)—, —C(=O)—, Si, and P.

Other features and aspects will be apparent from the following detailed description, the drawings, and the claims.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, the present invention will be described in more detail. Technical terms and scientific terms used in the present specification have the general meaning understood by those skilled in the art to which the present invention pertains unless otherwise defined, and a description for the known function and configuration obscuring the present invention will be omitted in the following description.

The term "carbene" used herein refers to a divalent carbon atom $$( *\overset{..}{\underset{}{C}} * )$$

having a structure including two bonds among four carbon bonds capable of binding with other atoms.

The terms "alkyl" and "alkoxy" used herein and a substituent containing alkyl refers to a functional group derived from a hydrocarbon in a straight chain or branched chain form. In addition, alkyl and a substituent including alkyl according to the present invention preferentially has a short chain of 1 to 7 carbon atoms, and may be preferably selected from the group consisting of methyl, ethyl, propyl, butyl, and the like, but not limited thereto. In addition, the alkoxy refers to *—O-alkyl.

The term "alkenyl" used herein refers to a functional group derived from a hydrocarbon in a straight chain or branched chain form containing one or more double bonds, and "alkynyl" refers to a functional group derived from a hydrocarbon in a straight chain or branched chain form containing one or more triple bonds.

The term "alkenyloxy" used herein refers to *—O-alkenyl, and "alkynyloxy" refers to *—O-alkynyl.

The term "alkylamino" used herein refers to a functional group including both monoalkylamino (*—NHR') or dialkylamino (*—NR'R"), and the alkyl is as defined above.

In addition, the term "cycloalkyl" used herein refers to a functional group derived from a completely saturated or partially unsaturated hydrocarbon ring having 3 to 9 carbon atoms and includes those to which aryl or heteroaryl is fused; and "heterocycloalkyl" refers to a free radical derived from a monocyclic or polycyclic non-aromatic ring containing 3 to 9 ring atoms containing one or more selected from the group consisting of B, N, O, S, Se, —P(=O)—, —C(=O)—, Si, P, and the like.

The term "aryl" used herein refers to a functional group derived from aromatic hydrocarbon by removal of one hydrogen, including a monocyclic or fused ring system containing suitably 4 to 9, preferably 5 or 6 ring atoms in each ring, and including even a form in which a plurality of aryls is linked by a single bond. As an example, phenyl, naphthyl, biphenyl, terphenyl, anthryl, indenyl, fluorenyl, phenanthryl, triphenylenyl, pyrenyl, perylenyl, chrysenyl, naphthacenyl, fluoranthenyl, and the like are included, but not limited thereto.

The term "heteroaryl" used herein refers to a functional group derived from an aromatic hydrocarbon by removal of one hydrogen, which is a functional group derived from a monocyclic or polycyclic aromatic hydrocarbon containing 4 to 9 ring atoms containing one or more selected from the group consisting of B, N, O, S, Se, —P(=O)—, —C(=O)—, Si, P, and the like, including a monocyclic or fused ring system containing suitably 4 to 9, preferably 5 or 6 ring atoms in each ring, and including even a form in which a plurality of heteroaryls is linked by a single bond. As an example, monocyclic heteroaryls such as furyl, thiophenyl, pyrrolyl, pyranyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pirazinyl, pirimidinyl, and piridazinyl; polycyclic heteroaryls such as benzofuranyl, benzothiophenyl, isobenzofuranyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinolizinyl, quinoxalinyl, carbazolyl, phenantridinyl, and benzodioxolyl; and the like are included, but not limited thereto.

In addition, the term "halogen" used herein refers to a fluorine (F), chlorine (Cl), bromine (Br), or iodine (I) atom.

In addition, the number of carbons according to the definition of the substituents described in Chemical Formula 1 herein does not include the number of carbons of the substituents which may be further substituted.

The present inventors extensively studied, from the understanding that the reactivity of the N-heterocyclic carbene compound is influenced by an HOMO-LUMO energy gap and singlet-triplet transition energy, and as a result, devised a coumaraz-2-on-4-ylidene-based compound which is the N-heterocyclic carbene compound having a new structure.

The coumaraz-2-on-4-ylidene-based compound has significantly low values as compared with the conventionally known N-heterocyclic carbene compound, in the HOMO-LUMO energy gap and the singlet-triplet transition energy, as well as the high reactivity. In particular, the coumaraz-2-on-4-ylidene-based compound greatly contributes to the nature as a ligand, thereby greatly changing the electrical/chemical stereostructure of the transition metal compound including a ligand derived therefrom.

Thus, the present disclosure provides the coumaraz-2-on-4-ylidene-based compound having a new carbene compound structure and a preparation method thereof. In addition, a transition metal compound including a ligand derived therefrom and a derivative to which various functional groups are introduced using the same as a reaction intermediate are provided, and also, it is intended that the use thereof is extended to applications as a catalyst composition or an organic electroluminescent element material using the same.

An embodiment of the present invention is a novel transition metal compound.

The transition metal compound according to an exemplary embodiment of the present invention may be represented by the following Chemical Formula 1:

[Chemical Formula 1]

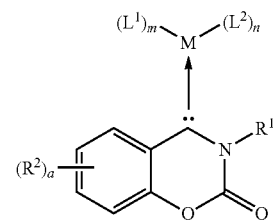

wherein

M is a transition metal;

m is an integer of 1 or 2, n is an integer of 0 to 2, and m+n+1 is an oxidation number of a used transition metal;

$L^1$ is a halogen;

$L^2$ is a monodentate ligand or a bidentate ligand;

a is an integer of 0 to 4;

$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocycloalkyl, $C_6$-$C_{30}$ aryl, and $C_6$-$C_{30}$ heteroaryl;

$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocycloalkyl, $C_6$-$C_{30}$ aryl, and $C_6$-$C_{30}$ heteroaryl, and when a is an integer of 2 or more, $R^1$ may be the same or different; and alkyl, alkenyl, alkynyl, cycloalkyl, heterocycloalkyl, aryl, or heteroaryl of $R^1$ and alkyl, alkenyl, alkynyl, alkoxy, alkenyloxy, alkynyloxy, alkylamino, cycloalkyl, heterocycloalkyl, aryl, or heteroaryl of $R^2$ may be independently of one another further substituted by one or more substituents selected from the group consisting of halogen, hydroxy, cyano, $C_1$-$C_{30}$ alkyl, and halo$C_1$-$C_{30}$ alkyl, and heterocycloalkyl or heteroaryl of $R^1$ and $R^2$ independently of each other contains one or more selected from the group consisting of B, N, O, S, Se, —P(=O)—, —C(=O)—, Si, and P.

The transition metal compound of Chemical Formula 1 includes a ligand derived from a coumaraz-2-on-4-ylidene-based compound which is an N-heterocyclic carbene compound having a new structure. The coumaraz-2-on-4-ylidene-based compound is abundant in electrons, and the ligand derived therefrom is capable of implementing flexible steric bulk and may increase an effect as a main ligand of the transition metal compound (transition metal complex). Due to the structural property as such, improved electrical/chemical properties may be implemented.

Specifically, the coumaraz-2-on-4-ylidene-based compound has a cycloalkylamino carbene structure having a carbonyl bonded to nitrogen in an adjacent position to carbene, and by having a fused benzene ring to the cycloalkylamino carbene structure, represents a lower value of the HOMO-LUMO energy gap and a significantly lower value of the singlet-triplet transition energy. That is, due to the structural property as such, strong interaction with the transition metal may be expected.

In the transition metal compound of Chemical Formula 1, M may be a transition metal of Groups 6 to 11 (for example, a metal having a d electron). Specifically, M may be a transition metal selected from the group consisting of Group 6 metals such as chromium (Cr), molybdenum (Mo), and tungsten (W); Group 7 metals such as manganese (Mn); Group 8 metals such as iron (Fe), ruthenium (Ru), and osmium (Os); Group 9 metals such as cobalt (Co), rhodium (Rh), and iridium (Ir); Group 10 metals such as nickel (Ni), palladium (Pd), and platinum (Pt); and Group 11 metals such as copper (Cu), silver (Ag), and gold (Au).

In the transition metal compound of Chemical Formula 1, M may be a transition metal having an oxidation number of +2 to +4.

As an example, M in Chemical Formula 1 may be a Group 9 transition metal selected from the group consisting of cobalt (Co), rhodium (Rh), iridium (Ir), and the like.

As an example, M in Chemical Formula 1 may be a Group 10 transition metal selected from the group consisting of nickel (Ni), palladium (Pd), platinum (Pt), and the like.

As an example, M in Chemical Formula 1 may be a Group 11 transition metal selected from the group consisting of copper (Cu), silver (Ag), gold (Au), and the like.

The transition metal compound of Chemical Formula 1 includes a ligand derived from the coumaraz-2-on-4-ylidene-based compound as a main ligand, and in terms of achieving a stable complex, may include an additional ligand. Herein, the additional ligand may correspond to $L^1$ and $L^2$ in Chemical Formula 1. $L^1$ is a halogen and at least one is included in Chemical Formula 1, and depending on the oxidation number of the transition metal to be used, $L^1$ may further include a monodentate or bidentate ligand.

In the transition metal compound of Chemical Formula 1, $L^2$ may be CO, nitrile, butadiene, pentadiene, hexadiene, cyclopentadiene, cyclohexadiene, cyclooctadiene, allyl, cyclohexene, cyclooctene, norbornadiene, or the like.

As an example, $L^2$ may be 1,3-cyclopentadiene, 1,3-cyclohexadiene, 1,4-cyclohexadiene, 1,3-cyclooctadiene, 1,4-cyclooctadiene, 1,5-cyclooctadiene, 2,5-norbornadiene, or the like.

In the transition metal compound of Chemical Formula 1, a may be an integer of 0 to 2; $R^1$ may be $C_1$-$C_{30}$ alkyl, $C_3$-$C_{30}$ cycloalkyl, or $C_1$-$C_{30}$ alkyl $C_6$-$C_{30}$ aryl; and $R^2$ may be $C_1$-$C_{30}$ alkoxy, $C_1$-$C_{30}$ alkylamino, halogen, or nitro.

Specifically, the transition metal compound may be at least one selected from the following structure, but not limited thereto:

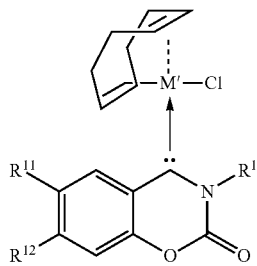

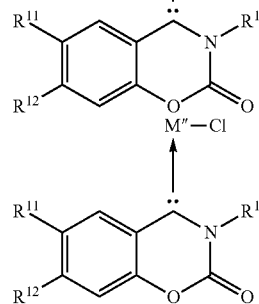

wherein

M' is a Group 9 transition metal;

M" is a Group 11 transition metal;

$R^{11}$ and $R^{12}$ are independently of each other hydrogen, $C_1$-$C_7$ alkoxy, $C_1$-$C_7$ alkylamino, halogen, or nitro; and $R^1$ is $C_1$-$C_7$ alkyl, $C_3$-$C_{12}$ cycloalkyl, or $C_1$-$C_7$ alkyl $C_6$-$C_{12}$ aryl.

As an example, M' in the above structure may be a Group 9 transition metal selected from the group consisting of cobalt (Co), rhodium (Rh), iridium (Ir), and the like.

As an example, M" in the above structure may be a Group 11 transition metal selected from the group consisting of copper (Cu), silver (Ag), gold (Au), and the like.

An embodiment of the present invention is a use of the transition metal compound.

According to an exemplary embodiment of the present invention, a catalyst composition including the transition metal compound of Chemical Formula 1 is provided.

The transition metal compound of Chemical Formula 1 which is a transition metal compound including a ligand derived from a coumaraz-2-on-4-ylidene-based compound having a new carbene compound structure, is abundant in electrons and also due to high reactivity, may be used as a catalyst for activating a carbon-hydrogen bond (C—H bond), a carbon-carbon bond (C—C bond), a carbon-nitrogen bond (C—N bond), and the like, in various organic synthesis reactions.

As an example, the transition metal compound may be used as a catalyst for a hydrogenation reaction of olefin, imine, and the like.

As an example, the transition metal compound may be used as a catalyst for an olefin metethesis reaction. Herein, the metethesis reaction may be a cyclization (ring closure) metathesis reaction.

As an example, the transition metal compound may be used as a catalyst for a cyclization reaction. Here, the cyclization reaction may be an olefin-alkyne cyclization reaction.

In addition, the transition metal compound of Chemical Formula 1 may further improve catalytic activity in the above-described reaction, by introducing a substituent of an electron withdrawing group.

In addition, according to an exemplary embodiment of the present invention, an organic electroluminescent element including the transition metal compound of Chemical Formula 1 is provided.

The transition metal compound of Chemical Formula 1 which is a transition metal compound including a ligand derived from a coumaraz-2-on-4-ylidene-based compound having a new carbene compound structure, is easily excited even by a wavelength of light having low energy to emit light, and shows excellence in a light emitting property. In addition, improved electrochemical properties (for example, a low HOMO-LUMO energy gap and singlet-triplet transition energy) are implemented, whereby improvement of lifespan characteristics of the organic electroluminescent element employing the transition metal compound is promoted.

As an example, the transition metal compound may be used as emitting materials, electron transport materials, hole transport materials, and the like of the organic electroluminescent element.

As an example, the transition metal compound is used as a dopant material or a host material among the emitting materials of the organic electroluminescent element, thereby implementing improved internal quantum efficiency and also showing a very high light emitting property.

An embodiment of the present invention is preparation method of the transition metal compound.

Specifically, the transition metal compound may be prepared by a preparation method including: reacting a compound of the following Chemical Formula A with a carbonate precursor to prepare a compound of Chemical Formula B and reacting a transition metal precursor in the presence of an organic base:

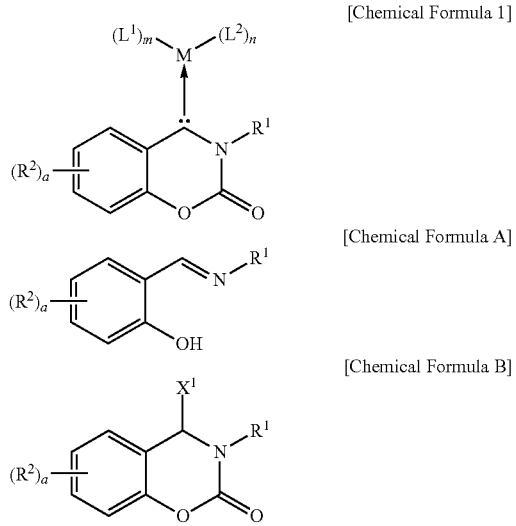

[Chemical Formula 1]

[Chemical Formula A]

[Chemical Formula B]

wherein
M is a transition metal;
m is an integer of 1 or 2, n is an integer of 0 to 2, and m+n+1 is an oxidation number of a used transition metal;
$L^1$ is a halogen;
$L^2$ is a monodentate ligand or a bidentate ligand;
$X^1$ is a halogen;
a is an integer of 0 to 4;
$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocycloalkyl, $C_6$-$C_{30}$ aryl, and $C_6$-$C_{30}$ heteroaryl;
$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocycloalkyl, $C_6$-$C_{30}$ aryl, and $C_6$-$C_{30}$ heteroaryl, and when a is an integer of 2 or more, $R^1$ may be the same or different; and alkyl, alkenyl, alkynyl, cycloalkyl, heterocycloalkyl, aryl, or heteroaryl of $R^1$ and alkyl, alkenyl, alkynyl, alkoxy, alkenyloxy, alkynyloxy, alkylamino, cycloalkyl, heterocycloalkyl, aryl, or heteroaryl of $R^2$ may be independently of one another further substituted by one or more substituents selected from the group consisting of halogen, hydroxy, cyano, $C_1$-$C_{30}$ alkyl, and halo$C_1$-$C_{30}$ alkyl, and heterocycloalkyl or heteroaryl of $R^1$ and $R^2$ independently of each other contains one or more selected from the group consisting of B, N, O, S, Se, —P(=O)—, —C(=O)—, Si, and P.

According to the preparation method as described above, the transition metal compound of Chemical Formula 1 may be synthesized in large quantities by a very simple method, and may be synthesized by a very economical method.

In the preparation method of the compound represented by Chemical Formula 1, the carbonate precursor may be one or a mixture of two or more selected from the group consisting of phosgene, diphosgene, triphosgene, bromophosgene, and the like. Here, the carbonate precursor may be used at 0.4 to 2.0 mol, based on 1 mol of the compound of Chemical Formula A. Specifically, the carbonate precursor may be used at 0.1 to 3.0 mol, and more specifically, at 0.4 to 2.0 mol, but not limited thereto.

As an example, when phosgene is used, it is preferred that the phosgene is used at 1.2 to 2.0 mol, based on 1 mol of the compound of Chemical Formula A.

As an example, when diphosgene is used, it is preferred that the diphosgene is used at 0.6 to 1.0 mol, based on 1 mol of the compound of Chemical Formula A.

As an example, when triphosgene is used, it is preferred that the triphosgene is used at 0.4 to 0.7 mol, based on 1 mol of the compound of Chemical Formula A.

In addition, a step of reacting the compound of Chemical Formula A with the carbonate precursor may be carried out in the presence of a weak base such as triethylamine, di-isopropylethylamine, and pyridine. Here, the weak base may be used at 1.0 to 5.0 mol, based on 1 mol of the compound of Chemical Formula A. Specifically, the weak base may be used at 1.2 to 3.0 mol, and more specifically, at 1.5 to 2.0 mol, but not limited thereto.

In the preparation method of the compound represented by Chemical Formula 1, the organic base is not limited as long as the organic base is a base having large steric hindrance, and as an example, lithium hexamethyldisilazide, sodium hexamethyldisilazide, potassium hexamethyldisilazane, lithium diisopropylamide, and the like may be included, but not limited thereto. Here, as the organic base, one or a mixed base of two or more selected from the above-listed organic bases may be used, of course. In addition, the organic base may be used at 1.0 to 2.0 mol, specifically 1.0 to 1.8 mol, and more specifically 1.0 to 1.4 mol, based on 1 mol of the compound of Chemical Formula B.

As an example, when the used amount of the organic base is out of the range described above and in excess, a large amount of by-products are produced as a side reaction, causing a difficulty in subsequent purification of the product, which is thus not preferred.

In the preparation method of the compound represented by Chemical Formula 1, the transition metal precursor is not limited as long as the transition metal precursor is an halide containing a transition metal, and as an example, $Na_2PdCl_4$, $PdCl_2$, $Pd(OAc)_2$, $RhCl_3$, $[Rh(COD)Cl]_2$, $IrCl_3$, [Ir(COD)

Cl]$_2$, Na$_2$PtCl$_4$, PtCl$_2$, AuCl$_3$, and the like may be included, and one or two or more selected from the listed halides may be used.

The preparation method of the compound of Chemical Formula 1 as described above may be performed under the condition in a very wide range, and is not limited to the reaction conditions such as a solvent, temperature, and time as described below, of course. In addition, mixing conditions such as an addition order or concentration of starting materials are also not limited separately.

Specifically, the preparation method of the compound of Chemical Formula 1 may be performed in a reaction medium including an organic solvent. Here, the organic solvent is not limited as long as the organic solvent may easily dissolve the starting materials, and as a non-limiting example thereof, hydrocarbon solvents such as butane, isobutane, pentane, hexane, heptane, octane, isooctane, nonane, decane, dodecane, cyclohexane, methylcyclohexane, benzene, toluene, and xylene; halogenated hydrocarbon-based solvents such as dichloromethane, trichloromethane, chloroethane, dichloroethane, and trichloroetehane; ether-based solvents such as tetrahydrofuran, 2-methyl tetrahydrofuran, dimethyl ether, diethyl ether, dipropyl ether, methylethyl ether, methylpropyl ether, and ethylpropyl ether; and the like may be included, but not limited thereto.

In addition, the step may be performed in a range of −80° C. to 30° C., and specifically in a range of −80° C. to room temperature (23° C.).

As an example, a step of reacting the compound of Chemical Formula A with the carbonate precursor in the step may be performed by adding the compounds at a low temperature (−78 to −20° C.) and then stirring them at room temperature for 3 to 20 hours.

As an example, after the step of reacting the compound of Chemical Formula A with the carbonate precursor, the temperature is lowered again to a low temperature, then a transition metal is reacted in the presence of an organic base, and stirring was performed at room temperature for 0.5 to 5 hours to prepare the transition metal compound of Chemical Formula 1.

In addition, in the step, after confirming that the starting materials are completely consumed by NMR or the like, the reaction is completed. When the reaction is completed, the organic solvent is distilled under reduced pressure after an extraction process, and then a desired product (for example, the carbene compound or the transition metal compound) may be separated and purified by a typical method such as column chromatography.

In addition, the step may be specifically performed under an inert gas atmosphere. The inert gas may be one or a mixture of two or more selected from the group consisting of nitrogen, helium, neon, argon, krypton, xenon, radon, and the like, but not limited thereto.

In addition, after this step, a step of injecting carbon monoxide into the reaction solution is further performed, thereby preparing a transition metal compound substituted with carbon monoxide.

As an example, the step of injecting carbon monoxide may be performed in a range of −10° C. to 30° C., and specifically the step may be performed in a range of 0° C. to room temperature (23° C.) for 10 to 100 minutes after carbon monoxide purging.

The preparation method of the compound represented by Chemical Formula 1 may be specifically performed as shown in the following Reaction Formulae 1 and 2. The more details are described in the following Examples. In addition, the preparation method of the transition metal compound according to the present invention is not limited to the following Reaction Formulae, and the compound may be synthesized by various methods using a known organic reaction, of course:

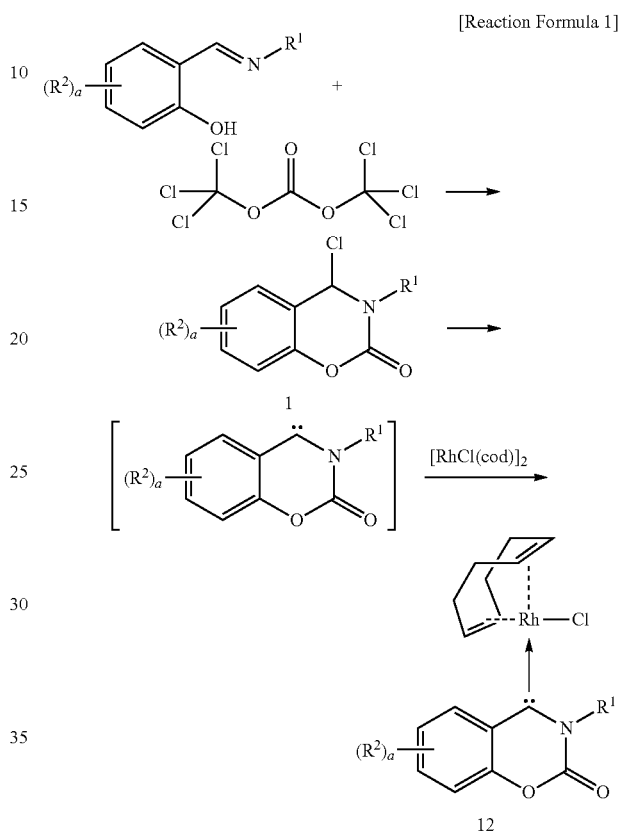

[Reaction Formula 1]

wherein the substituents are as defined in Chemical Formula 1;

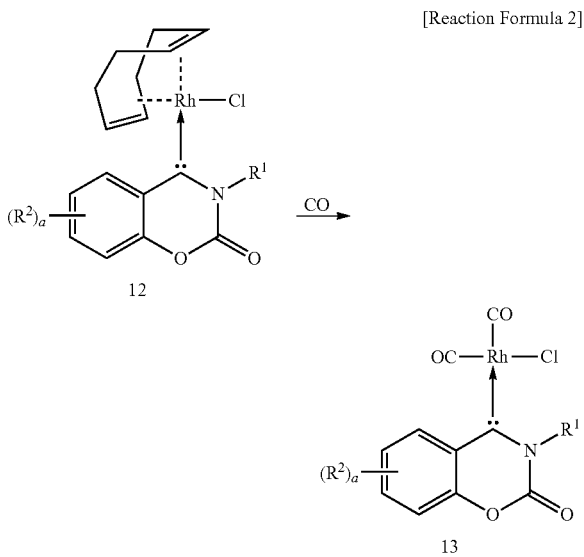

[Reaction Formula 2]

wherein the substituents are as defined in Chemical Formula 1.

An embodiment of the present invention is a novel carbene compound.

The carbene compound according to an exemplary embodiment of the present invention may be represented by the following Chemical Formula 2:

[Chemical Formula 2]

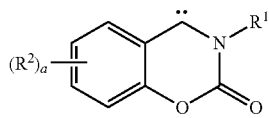

wherein a is an integer of 0 to 4;

$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocycloalkyl, $C_6$-$C_{30}$ aryl, and $C_6$-$C_{30}$ heteroaryl;

$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocycloalkyl, $C_6$-$C_{30}$ aryl, and $C_6$-$C_{30}$ heteroaryl, and when a is an integer of 2 or more, $R^1$ may be the same or different; and alkyl, alkenyl, alkynyl, cycloalkyl, heterocycloalkyl, aryl, or heteroaryl of $R^1$ and alkyl, alkenyl, alkynyl, alkoxy, alkenyloxy, alkynyloxy, alkylamino, cycloalkyl, heterocycloalkyl, aryl, or heteroaryl of $R^2$ may be independently of one another further substituted by one or more substituents selected from the group consisting of halogen, hydroxy, cyano, $C_1$-$C_{30}$ alkyl, and halo$C_1$-$C_{30}$ alkyl, and heterocycloalkyl or heteroaryl of $R^1$ and $R^2$ independently of each other contains one or more selected from the group consisting of B, N, O, S, Se, —P(=O)—, —C(=O)—, Si, and P.

In the carbene compound of Chemical Formula 2, a may be an integer of 0 to 2; $R^1$ may be $C_1$-$C_{30}$ alkyl, $C_3$-$C_{30}$ cycloalkyl, or $C_1$-$C_{30}$ alkyl $C_6$-$C_{30}$ aryl; and $R^2$ may be $C_1$-$C_{30}$ alkoxy, $C_1$-$C_{30}$ alkylamino, halogen, or nitro.

In the carbene compound of Chemical Formula 2, a may be an integer of 0 to 2; $R^1$ may be $C_1$—C alkyl, $C_3$-$C_{12}$ cycloalkyl, or $C_1$-$C_1$ alkyl $C_6$-$C_{12}$ aryl; and $R^2$ may be $C_1$-$C_7$ alkoxy, $C_1$-$C_7$ alkylamino, halogen, or nitro.

Specifically, the carbene compound of Chemical Formula 2 may be represented by the following Chemical Formula 3:

[Chemical Formula 3]

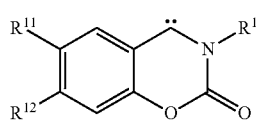

wherein $R^{11}$ and $R^{12}$ are independently of each other hydrogen, $C_1$-$C_7$ alkoxy, $C_1$-$C_7$ alkylamino, halogen, or nitro; and $R^1$ is $C_1$-$C_7$ alkyl, $C_3$-$C_{12}$ cycloalkyl, or $C_1$-$C_7$ alkyl $C_6$-$C_{12}$ aryl.

More specifically, the carbene compound of Chemical Formula 2 may be at least one selected from the following structures, but not limited thereto:

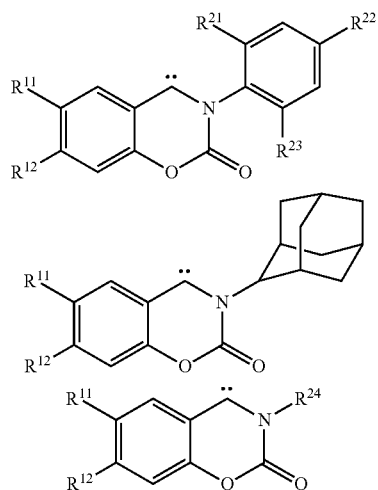

wherein $R^{11}$ and $R^{12}$ are independently of each other hydrogen, $C_1$-$C_7$ alkoxy, $C_1$-$C_7$ alkylamino, halogen, or nitro;

$R^{21}$ to $R^{23}$ are independently of one another hydrogen or $C_1$—C alkyl; and $R^{24}$ is $C_1$-$C_7$ alkyl or $C_3$-$C_{12}$ cycloalkyl.

Hereinafter, the present invention will be specifically described through the following Examples.

Prior to that, terms and words used in the present specification and claims are not to be construed as a general or dictionary meaning but are to be construed as meaning and concepts meeting the technical ideas of the present invention based on a principle that the inventors can appropriately define the concepts of terms in order to describe their own inventions in best mode. Therefore, the configurations illustrated in the Examples and drawings described herein are merely the most preferred exemplary embodiment of the present invention but do not represent all of the technical spirit of the present invention. Thus, it should be understood that there are various equivalents and modified examples to replace them at the time of filing the present application.

Unless otherwise stated, synthesis of all compounds was performed using a standard Schlenk or a glove box under a nitrogen atmosphere, and an organic solvent used in the reaction was used after being distilled immediately before use by refluxing the solvent under sodium metal and benzophenone to remove moisture therefrom.

Example 1

Step 1:

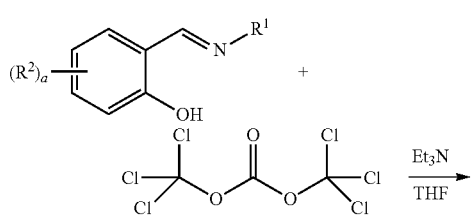

-continued

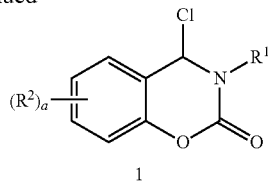

1

In a glove box under a nitrogen atmosphere, salicylimine (1.0 mmol, 1.0 eq.) and triethylamine (2.0 mmol, 2.0 eq.) were added to a 20 ml vial, and cold tetrahydrofuran (THF, 10 mL, −78° C.) was further added. A triphosgene solution (0.4 mmol, 0.4 eq., 2 mL of THF) was slowly added to the vial under a condition of −78° C., the temperature was raised to room temperature (23° C.), and stirring was performed for 12 hours. The reaction solution was filtered through celite, and the obtained solution was distilled under vacuum. The solid obtained by vacuum distillation was redissolved in toluene and then filtered through celite, and the solution was distilled under vacuum to obtain Compound 1.

1a ($R^1$=Dipp, $R^2$=H) 12.2 g (quant./10 g scale), $^1$H NMR (500 MHz, CDCl$_3$, 23° C.): δ=7.50 (td, $J_1$=7.7 Hz, $J_2$=1.6 Hz, 1H), 7.43 (t, J=7.7 Hz, 1H), 7.37 (td, $J_1$=7.7 Hz, $J_2$=1.3 Hz, 1H), 7.29 (td, $J_1$=7.1 Hz, $J_2$=1.0 Hz, 2H), 7.25 (d, J=7.5 Hz, 1H), 6.63 (s, 1H), 3.25-2.70 (br, 2H), 1.28 (d, J=6.0 Hz, 6H), 1.20 (br, 6H) ppm. $^1$H NMR (500 MHz, C$_6$D$_6$, 23° C.): δ=7.21 (d, J=4.0 Hz, 1H), 6.97 (t, J=4.5 Hz, 1H), 6.78 (t, J=6.5 Hz, 1H), 6.75 (td, $J_1$=6.5 Hz, $J_2$=1.5 Hz, 1H), 6.43 (s, 1H), 3.62 (m, 1H), 2.58 (m, 1H), 1.45 (d, J=6.7 Hz, 3H), 1.42 (d, J=6.7 Hz, 3H), 0.90 (d, J=6.7 Hz, 3H), 0.82 (d, J=6.7 Hz, 3H) ppm. $^{13}$C{$^1$H} NMR (125 MHz, CDCl$_3$, 23° C.): δ=149.91, 148.81, 134.18, 131.57, 130.09, 125.96, 125.43, 120.11, 117.22, 77.12, 29.17, 24.83 ppm. $^{13}$C{$^1$H} NMR (125 MHz, C$_6$D$_6$, 23° C.): δ=150.55, 149.15, 148.56, 144.94, 135.18, 131.44, 130.18, 125.70, 125.61, 125.07, 124.61, 120.95, 117.12, 77.98, 29.83, 24.86, 24.76, 24.35, 22.79 ppm. HRMS (EI): m/z calculated for C$_{20}$H$_{22}$ClNO$_2$ [M]$^+$ 343.1339, found 343.1335.

Step 2:

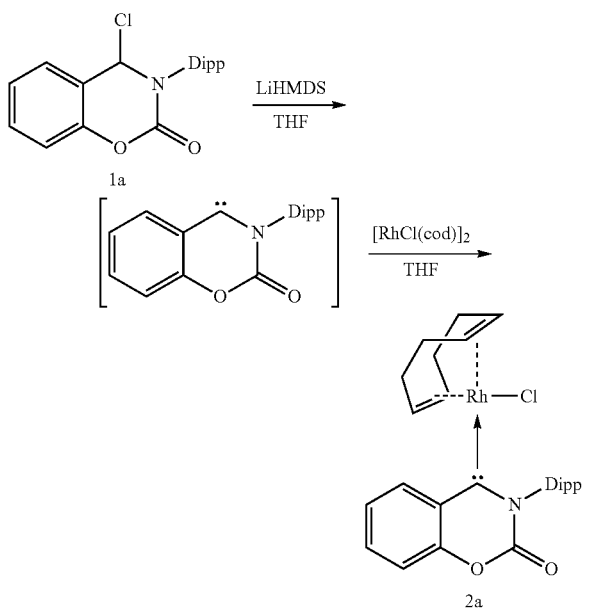

Dipp: 2,6-diisopropylphenyl

In a glove box under a nitrogen atmosphere, compound 1a (10.0 mg, 0.029 mmol), [RhCl(cod)]$_2$ (7.2 mg, 1.00 eq.), and lithium hexamethyldisilazide (LiHMDS, 5.1 mg, 1.05 eq.) were added to a 4 ml vial, and cold tetrahydrofuran (THF, 3 mL, −78° C.) was further added. A triphosgene solution (0.4 mmol, 0.4 eq., 2 mL of THF) was slowly added to the vial under a condition of −78° C., and stirring was performed for 2 hours. Thereafter, the reactant was heated to room temperature (23° C.) and stirred for 1 hour. After the reaction solution was concentrated, the solution was purified by column chromatography (hexane:ethyl acetate=3:1, wt:wt) to obtain transition metal compound 2a.

12a ($R^1$=Dipp, $R^2$=H) 28 mg (5%), $^1$H NMR (500 MHz, CDCl$_3$, 23° C.): δ=9.68 (dd, $J_1$=8.0 Hz, $J_2$=1.6 Hz, 1H), 7.80 (td, J=7.6 Hz, $J_2$=1.7 Hz, 1H), 7.62 (td, J=7.8 Hz, $J_2$=1.0 Hz, 1H), 7.60-7.53 (m, 2H), 7.29-7.25 (m, 2H), 5.39 (q, J=8.0 Hz, 1H), 5.18 (m, 1H), 3.88 (m, 1H), 3.67 (m, 1H), 2.88 (m, 1H), 2.67 (m, 1H), 2.18 (m, 2H), 2.00 (m, 2H), 1.78 (m, 1H), 1.54 (d, J=6.5 Hz, 3H), 1.43 (m, 1H), 1.17 (d, J=6.9 Hz, 3H), 1.11 (t, J=6.9 Hz, 6H) ppm. $^{13}$C{$^1$H} NMR (125 MHz, CDCl$_3$, 23° C.): δ=273.95 (d, J=43.9 Hz), 147.93, 145.42, 144.12, 142.58, 141.99, 138.93, 137.18, 130.47, 127.93, 126.21, 125.71, 123.51, 116.14, 106.22 (d, J=6.3 Hz), 106.05 (d, J=4.8 Hz), 72.37 (d, J=14.1 Hz), 71.52 (d, J=13.8 Hz), 34.69, 30.17, 29.40, 29.29, 29.14, 26.57, 26.00, 25.18, 24.15, 22.70 ppm. HRMS (FAB): m/z calculated for C$_{23}$H$_{32}$ClNO$_2$Rh [M+H]$^+$ 553.1255, found 553.1252.

Examples 2 to 10

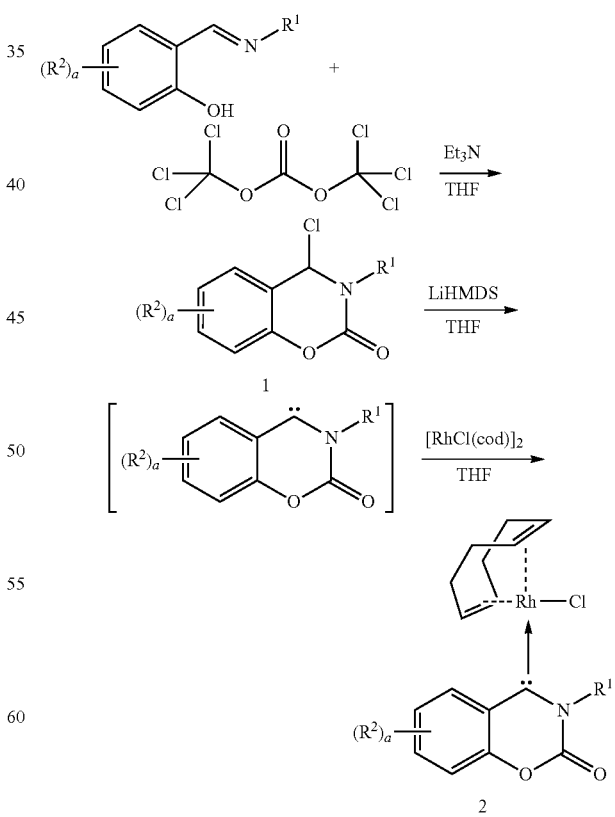

Compounds 1b to 1j were prepared in a similar manner to the preparation method of Example 1, and a transition metal compound was prepared. The Data of obtained compounds 1b to 1j and transition metal compound 2j are shown in the following Table 1:

TABLE 1

| Compound | Structure of compound | Data |
|---|---|---|
| 1b | $R^1$ = Mes, $R^2$ = H | 300 mg (quant.), $^1$H NMR (500 MHz, CDCl$_3$, 23° C.): δ = 7.47 (td, J1 = 7.8 Hz, J2 = 1.5 Hz, 1H), 7.38 (dd, J1 = 7.8 Hz, J2 = 1.3 Hz, 1H), 7.27 (td, J1 = 7.5 Hz, J2 = 1.0 Hz, 1H), 7.22 (d, J = 8.0 Hz, 1H), 6.99 (s, 2H), 6.73 (s, 1H), 2.31 (s, 3H), 2.28 (br, 6 H) ppm, $^1$H NMR (500 Hz, C$_6$D$_6$, 23° C.): δ = 6.78-6.75 (m, 4H), 6.69-6.65 (m, 1H), 6.61 (s, 1H), 6.32 (s, 1H), 2.62 (s, 3H), 2.06 (s, 3H), 1.61 (s, 3H) ppm. $^{13}$C{$^1$H} NMR (125 MHz, CDCl$_3$, 23° C.): δ = 149.88, 148.10, 139.20, 134.43, 131.55, 130.22, 126.04, 125.40, 119.94, 117.12, 76.60, 21.13 ppm. $^{13}$C{$^1$H} NMR (125 MHz, C$_6$D$_6$, 23° C.): δ = 150.18, 147.21, 138.33, 137.82, 135.05, 133.79, 130.92, 130.28, 129.42, 125.38, 124.53, 120.39, 116.65, 77.14, 20.53, 19.24, 17.26 ppm HRMS (EI): m/z calculated for C17H16ClNO2 [M]+ 301.0870, found 301.0867. |
| 1c | $R^1$ = Ad, $R^2$ = H | 317 mg (quant.), $^1$H NMR (500 MHz, CDCl$_3$, 23° C.): δ = 7.39 (td, J1 = 7.5 Hz, J2 = 1.5 Hz, 1H), 7.31 (dd, J1 = 7.5 Hz, J2 = 1.5 Hz, 1H), 7.19 (t, J = 7.5 Hz, 1H), 7.12 (d, J = 8.0 Hz, 1H), 6.99 (s, 1H), 2.37 (d, J = 2.5 Hz, 6H), 2.22 (s, 3H), 1.75 (q, J1 = 13.0 Hz, 6H) ppm. $^{13}$C{$^1$H} NMR (125 MHz, CDCl$_3$, 23° C.): δ = 149.68, 148.03, 131.12, 125.18, 124.71, 121.31, 116.19, 72.00, 61.70, 39.15, 36.24, 30.27 ppm. HRMS (EI): m/z calculated for C18H20ClNO2 [M-H]+ 316.1104, found 316.1107. |
| 1d | $R^1$ = $^t$Bu, $R^2$ = H | 239 mg (quant.), $^1$H NMR (500 MHz, CDCl$_3$, 23° C.): δ = 7.40 (td, J1 = 8.0 Hz, J2 = 1.5 Hz, 1H), 7.32 (dd, J1 = 8.0 Hz, J2 = 1.5 Hz, 1H), 7.20 (td, J1 = 7.5 Hz, J2 = 1.0 Hz, 1H), 7.12 (d, J = 8.0 Hz, 1H), 6.97 (s, 1H), 1.65 (s, 9H) ppm. $^{13}$C{$^1$H} NMR (125 MHz, CDCl$_3$, 23° C.): δ = 149.71, 148.43, 131.20, 125.29, 124.79, 121.14, 116.25, 72.90, 60.47, 27.97 ppm. HRMS (EI): m/z calculated for C12H14ClNO2 [M-CH3]+ 224. C 478, found. 224.0480. |
| 1e | $R^1$ = Dipp, $R^2$ = 6-NO$_2$ | 387 mg (quant.), $^1$H NMR (500 MHz, C$_6$D$_6$, 23° C.): δ = 7.76 (d, J1 = 2.6 Hz, 1H), 7.41 (dd, J1 = 9.1 Hz, J2 = 2.5 Hz, 1H), 7.19 (q, J = 8.2 Hz, 1H), 7.18 (d, J = 2.1 Hz, 1H), 6.96 (dd, J1 = 7.2 Hz, J2 = 2.0 Hz, 1H), 6.33 (d, J = 9.15 Hz, 1H), 6.11 (s, 1H), 3.47 (m, 1H), 2.44 (m, 1H), 1.41 (d, J = 6.8 Hz, 3H), 1.38 (d, J = 6.8 Hz, 3H), 0.91 (d, J = 6.8 Hz, 3H), 0.85 (d, J = 6.8 Hz, 3H) ppm. $^{13}$C{$^1$H} NMR (125 MHz, C$_6$D$_6$, 23° C.) δ = 153.87, 148.49, 147.26, 144.56, 134.42, 130.53, 129.33, 128.56, 126.76, 125.88, 124.62, 121.28, 117.89, 75.81, 29.85, 29.31, 24.83, 24.64, 24.29, 22.59 ppm HRMS (EI): m/z calculated for C20H21ClN2O4 [M]+ 388.1190, found 388.1188. |
| 1f | $R^1$ = Dipp, $R^2$ = 6-Cl | 377 mg (quant.), $^1$H NMR (500 MHz, CDCl$_3$, 23° C.): δ = 7.44 (m, 2H), 7.35 (d, J = 2.4 Hz, 1H), 7.33 (m, 1H), 7.24 (m, 1H), 7.20 (d, J. = 8.8 Hz, 1H), 6.54 (s, 1H), 3.25 (m, 1H), 2.60 (m, 1H), 1.29 (m, 3H), 1.04 (d, J = 6.5 Hz, 3H) ppm. $^{13}$C{$^1$H} NMR (125 MHz, CDCl3, 23° C.): δ = 148.58, 148.42, 148.31, 144.49, 133.90, 131.78, 130.62, 130.26, 125.69, 125.58, 124.74, 121.45, 118.78, 75.96, 29.45, 29.00, 25.13, 24.50, 24.29, 23.35 ppm. $^1$H NMR (500 MHz, C$_6$D$_6$, 23° C.): 7.19 (m, 2H), 6.96 (dd, J1 = 6.4 Hz, J2 = 2.9, 1H), 2.37 (d, J = 2.4 Hz, 1H), 6.65 (dd, J1 = 8.9 Hz, J2 = 2.4 Hz, 1H), 6.44 (d, J = 8.9 Hz, 1H), 6.24 (s, 1H), 3.54 (m, 1H), 2.52 (m, 1H), 1.41 (dd, J1 = 16.1 Hz, J2 = 6.8 Hz, 6H), 0.87 (dd, J1 = 25.2 Hz, J2 = 6.83 Hz, 6H) $^{13}$C{$^1$H} NMR (125 MHz, C$_6$D$_6$, 23° C.): δ = 149.09, 148.92, 148.06, 144.79, 134.83, 131.64, 130.32, 125.78, 125.17, 124.61, 122.24, 118.68, 76.72, 29.83, 29.20, 24.84, 24.69, 24.31, 22.71 ppm. HRMS (EI): m/z calculated for C20H21Cl2NO2 [M]+ 377.0949, found 377.0945. |
| 1g | $R^1$ = Dipp, $R^2$ = 7-Cl | 377 mg (quant.), $^1$H NMR (500 MHz, C$_6$D$_6$, 23° C.): δ = 7.21 (d, J = 4.1 Hz, 1H), 7.20 (s, 1H), 6.98 (dd, J1 = 6.4 Hz, J2 = 3.0 Hz, 1H), 6.63 (dd, J1 = 8.3 Hz, J2 = 2.0 Hz, 1H), 6.41 (d, j = 8.3 Hz, 1H), 6.29 (s, 1H), 3.55 (m, 1H), 2.54 (m, 1H), 1.42 (d, J = 6.8 Hz, 3H), 1.41 (d, J = 6,7 Hz, 3H), 0.93 (d, J = 6.9 Hz, 3H), 0.86 (d, J = 6.8 Hz, 3H) ppm. $^{13}$C{$^1$H} NMR (125 MHz, C$_6$D$_6$, 23° C.): δ = 150.87, 149.09, 147.87, 144.77, 137.09, 134.92, 130.31, 126.46, 125.79, 125.49, 124.63, 119.32, 117.64, 77.12, 29.82, 29,16, 24.85, 24.70, 24.30, 22.81 ppm. HRMS (EI): m/z calculated for C20H21Cl2NO2 [M]+ 377.0949, found 377.0952. |
| 1h | $R^1$ = Dipp, $R^2$ = 6-OMe | 372 mg (quant.), $^1$H NMR (500 MHz, CDCl$_3$, 23° C.): δ = 7.42 (t, J = 7.8 Hz, 1H), 7.28 (d, J = 7.8 Hz, 3H), 7.17 (d, J = 9.1 Hz, 1H), 7.03 (dd, J1 = 9.1 Hz, J2 = 2.9 Hz, 1H), 6.82 (d, J = 2.9 Hz, 1H), 6.58 (s, 1H), 3.85 (s, 3H), 2.97 (br, 2H), 1.29 (d, J = 6.8 Hz, 6H), 1.17 (br, 6H) ppm. $^{13}$C{$^1$H} NMR (125 MHz, CDCl$_3$, 23° C.): δ = 156.87, 149.03, 143.79, 134.23, 130.06, 125.08, 120.48, 118.26, 117.91, 109.70, 77.36, 56.05, 29.15, 24.83, 23.83 ppm. $^1$H NMR (500 MHz, C$_6$D$_6$, 23° C.): δ = 7.22 (m, 2H), 6.99 (m, 1H), 6.74 (d, J = 9.1 Hz), 6.56 (d, J = 2.9 Hz, 1H), 6.44 (s, 1H), 6.42 (dd, J1 = 9.1 Hz, J2 = 2.9 Hz, 1H), 3.65 (m, 1H), 3.08 (s, 3H), 2.65 (m, 1H), 1.45 (dd, J1 = 13.8, J2 = 6.9, 6H), 0.91 (dd, J1 = 31.6 Hz, J2 = 6.9 Hz, 6H) ppm. $^{13}$C{$^1$H} NMR (125 MHz, C$_6$D$_6$, 23° C.): δ = 156.94, 149.24, 148.84, 144.93, 144.43, 135.29, 130.14, 125.72, 124.54, 121.53, 118.25, 117.50, 109.76, 78.29, 55.20, 29.85, 29.19, 24.79, 24.39, 22.77 ppm. HRMS (EI): m/z calculated for C21H24ClNO3 [M]+ 373.1445, found 373.1442. |
| 1i | $R^1$ = Dipp, $R^2$ = 7-OMe | 372 mg (quant.), $^1$H NMR (500 MHz, CDCl$_3$, 23° C.): δ = 7.42 (t, j = 7.8 Hz, 1H), 7.27 (d, J = 8.1 Hz, 2H), 6.83 (dd, J1 = 8.5 Hz, J2 = 2.4 Hz, 1H), 6.73 (d., J = 2.6 Hz, 1H), 6.62 (s, 1H), 3.87 (s, 3H), 2.97 (m, 2H), 1.28 (d, J = 6.7 Hz, 6H), 1.17 (d, J = 6.8 Hz, 6H) ppm. $^{13}$C{$^1$H} NMR (125 MHz, CDCl$_3$, 23° C.) δ = 162.23, 151.25, 148.75, 146.59, 134.29, 130.06, 126.98, 125.05, 112.68, 112.19, 101.61, 77.86, 55.93, 29.15, 24.86, 23.80 ppm. HRMS (FAB): m/z calculated for C21H24ClNO3 [M-Cl]+ 338.1756, found 338.1755. |
| 1j | $R^1$ = Dipp, $R^2$ = 7-NEt$_2$ | 458 mg (quant. with 1 eq. of THF), $^1$H NMR (500 MHz, CDCl$_3$, 23° C.): δ = 9.52 (s, 1H), 8.82 (d, J = 9.0 Hz, 1H), 7.50 (t, J = 7.9 Hz, 1H), 7.31-7.27 (d + d, J = 7.9 Hz, 3H), 6.64 (s, 1H), 3.51 (s, 6H), 2.70 (m, 2H), 1.27 (d, j = 6.7 Hz, 6H), 1.18 (d, J = 6.8 Hz, 6H) ppm. $^{13}$C{$^1$H} NMR (125 MHz, CDCl$_3$, 23° C.): δ = 161.23, 159.33, 145.19, 144.52, 137.21, 132.97, 131.70, 125.20, 116.16, 107.39, 97.76, 77.37, 42.60, 29.38, 24.24, 23.95 ppm. HRMS (FAB): m/z |

TABLE 1-continued

| Compound | Structure of compound | Data |
|---|---|---|
| 2j | $R^1$ = Dipp, $R^2$ = 7-NMe$_2$ | calculated for C22H27ClN2O2 [M—Cl]+ 351.2073, found 351.2075.<br>68 mg (23%, 0.5 mmol scale), $^1$H NMR (500 MHz, CDCl$_3$, 23° C.): δ = 9.38 (d, J = 9.1 Hz, 1H), 7.23 (dd, J$_1$ = 7.0 Hz, J$_2$ = 2.3 Hz, 1H), 6.89 (dd, J$_1$ = 9.2 Hz, J$_2$ = 2.6 Hz, 1H), 6.24 (d, J = 2.7 Hz, 1H), 5.16 (q, J = 8.0 Hz, 1H), 5.02 (m, 1H), 3,75 (m, 1H), 3.71 (m, 1H), 3.18 (s, 6H), 2.73 (m, 1H) , 2.63 (m, 1H), 2.26 (m, 1H), 2.11 (m, 2H), 1.95 (m, 2H), 1.66 (m, 1H), 1.53 (d, J = 6.6 Hz, 3H), 1,37 (m, 2H), 1.14 (d, J = 7.0 Hz, 3H), 1.12 (d, J = 6.9 Hz, 3H), 1.11 (d, J = 7.0 Hz, 3H) ppm. $^{13}$C{$^1$H} NMR (125 MHz, CDCl$_3$, 23° C.): δ = 258.40 (d, J = 43.7 Hz), 156.62, 149.23, 147.91, 144.49, 143.95, 142.85, 139.01, 129.99, 125.41, 123.43, 118.86, 110.80, 103.04 (d, J = 5.6 Hz) 102.78 (d, J = 5.7 Hz), 94.69, 71.48 (d, J = 15.0 Hz), 69.05 (d, J = 13.9 Hz), 40.56, 35.11, 29.92, 29.68, 29.18, 29.01, 28.50, 26.51, 26.04, 25.24, 24.52, 24.04, 22.88 ppm. HRMS (FAB): m/z calculated for C$_{30}$H$_{37}$ClN$_2$O$_2$Rh [M + H]+ 596.1677, found 596.1681. |

*Mes: 1,3,5-trimethyl-2-phenyl
*Dipp: 2,6-diisopropylphenyl
*Ad: adamantyl
*$^t$Bu: tert-butyl Examples 11 and 12

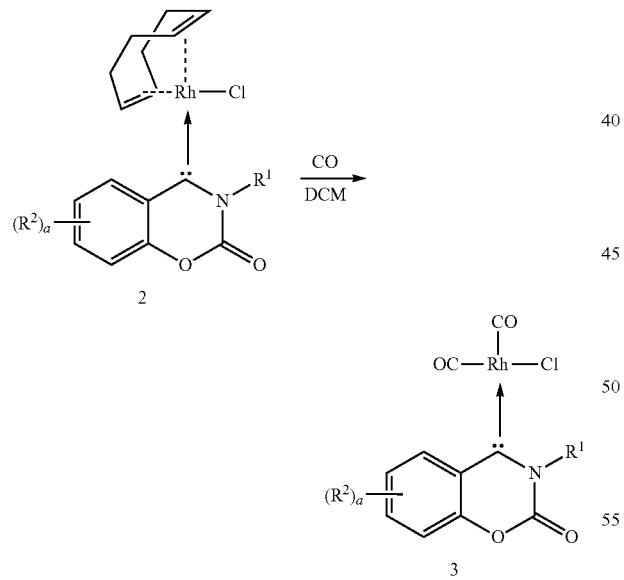

In a glove box under a nitrogen atmosphere, transition metal compound 2 (10.0 mg, 0.162 mmol) was added to a 4 ml vial, and cold dichloromethane (DCM, 2 mL, 0° C.) was further added. At room temperature, CO gas was purged in the reaction solution for 30 minutes. Thereafter, the thus-obtained solution was distilled under vacuum. The solid obtained by vacuum distillation was washed with hexane to obtain transition metal compound 3.

The data of obtained transition metal compound 3a and 3j are shown in the following Table 2:

TABLE 2

| Compound | Structure of compound | Data |
|---|---|---|
| 3a | $R^1$ = Dipp, $R^2$ = H | 18 mg (72%), IR (ATR): 2083 (s, C—O stretch), 1994 (s, C—O stretch) cm$^{-1}$, $^1$H NMR (500 MHz, CDCl$_3$, 23° C.): δ = 9.17 (t, J$_1$ = 8.0 Hz, J$_2$ = 1.6 Hz, 1H), 7.96 (td, J$_1$ = 7.9 Hz, J$_2$ = 1.5 Hz, 1H), 7.63 (td, J$_1$ = 7.6 Hz, J$_2$ = 0.9 Hz, 1H), 7.59 (t, J = 7.8 Hz, 1H), 7.44 (dd, J$_1$. = 8.0 Hz, J$_2$ = 1.4 Hz, 1H), 7.41 (d, J = 8.3 Hz, 1H), 7.35 (dd, J$_1$ = 7.8 Hz, J$_2$ = 1.3 Hz, 1H), 3.10 (m, 1H) , 2.55 (m, 1H) , 1.40 (d, J = 6.6 Hz, 3H), 1.31 (d, J = 6.7 Hz, 3H), 1.14 (d, J = 1.7 Hz, 3H), 1.12 (d, J = 1.6 Hz, 3H) ppm. $^{13}$C{$^1$H} NMR (125 MHz, CDCl$_3$, 23° C.) δ = 260.10 (d, J = 39.41 Hz), 185.52 (d, J = 52.02 Hz), 182.46 (d, J = 76.39 Hz), 148.88, 146.52, 143.00, 142.91, 142.30, 140.43, 139.12, 131.29, 128.84, 12.6.55, 125.71, 124.70, 116.02, 29.31, 29.26, 25.54, 25.30, 24.21, 22.56 ppm. HRMS (FAB): m/z calculated for C$_{22}$H$_{21}$ClNO$_4$Rh [M-C$_2$O$_2$RhCl + H]+ 308.650, found 308.1650 |
| 3j | $R^1$ = Dipp, $R^2$ = 7-NMe$_2$ | 24 mg ( 88%), IR (ATR): 2077 (s, C—O stretch), 1994 (s, C—O stretch) cm$^{-1}$, $^1$H NMR (500 MHz, CDCl$_3$, 23° C.): δ = 8.75 (d, J = 9.3 Hz, 1H), 7.52 (t, J = 7 . 8 Hz, 1H), 7.38 (dd, J$_1$ = 7.8 Hz, J$_2$ = 1.3 Hz, 1H), 7.31 (dd, J$_1$ = 7.8 Hz, J$_2$ = 1.3 Hz, 1H), 6.83 (dd, J$_1$ = 9.3 Hz, J$_2$ = 2.5 Hz, 1H), 6.33 (dd, J = 2.7 Hz, 1H), 3.26 (s, 6H), 3.16 (m, 1H), 2.67 (m, 1H) , 1.39 (d, J = 6.7 Hz, 3H), 1.31 (d, J = 6.7 Hz, 3H), 1.13 (d, J = 6.7 Hz, 3H), 1.11 (d, J = 6.8 Hz, 3H) ppm. $^{13}$C{$^1$H} NMR (125 MHz , CDCl$_3$, 23° C. ): δ = 240.09 (d, J = 38.78 Hz), 186.02 (d, J = 52.02 Hz), 183.07 (d, J = 76.53 Hz), 158.41, 152.77, 146..79, 143.82, 143.44, 139.01, 130.61, 128.83, 125.29, 124.36, 117.40, 111.21, 94.71, 40,89, 28.17, 25.54, 25.35, 24.13, 22.72, ppm. |

In addition, the electrochemical properties of the coumaraz-2-on-4-ylidene-based compound which is the N-heterocyclic carbene compound in Example 1 and the conventional N-heterocyclic carbene compound were confirmed. Herein, the electrochemical properties were calculated by a density functional theory (DFT), using Gaussian09.

TABLE 3

| | Example 1 | IPr | cAAC | 6-DAC | cAArC |
|---|---|---|---|---|---|
| S/T Gap (kcal/mol) | 26.7 | 81.4 | 47.5 | 42.3 | 39.5 |
| HOMO (eV) | −5.96 | −5.97 | −5.44 | −6.23 | −5.58 |
| LUMO (eV) | −2.43 | −0.46 | −0.43 | −2.2 | −1.47 |

As shown in the above Table 3, the compound according to the present invention has a low value of the HOMO-LUMO energy gap simultaneously with a significantly low value of singlet-triplet transition energy. Thus, the transition metal compound derived from the coumaraz-2-on-4-ylidene-based compound may be expected to have strong interaction with a transition metal.

However, IPr, cAAC, and cAArC which are a kind of conventional N-heterocyclic carbon compound has a high HOMO value but also has a high LUMO value, which makes strong I-backdonation interaction with a transition metal difficult. Moreover, it was confirmed that 6-DAC has a low LUMO value so that strong l-backdonation interaction was expected, but also has a very low HOMO value so that strong interaction with a transition metal may not be expected.

Accordingly, the transition metal compound derived from the coumaraz-2-on-4-ylidene-based compound is expected to show better electrochemical properties, with significant interaction with a transition metal, as compared with the transition metal compound derived from the conventional N-heterocyclic carbene compound.

According to the present invention, a new N-heterocyclic carbene compound having a low HOMO-LUMO energy gap and low singlet-triplet transition energy as compared with a conventional carbene compound may be provided. Thus, the N-heterocyclic carbene compound may be used as a ligand capable of effectively stabilizing a transition metal compound.

In addition, the N-heterocyclic carbene compound according to the present invention may allow activation of a carbon-hydrogen bond (C—H bond) for introducing a functional group of various embodiments with high reactivity or may participate in a [2+1]-cyclization addition reaction with olefin, and may trap olefin, isocyanide, sulfur, or selenium to be used as an intermediate of a coumaraz-2-on-4-ylidene-based compound of various embodiments.

In addition, according to the present invention, an N-heterocyclic carbene compound may be provided by a very simple method, and the transition metal compound containing a ligand derived therefrom may be synthesized in large quantities in a high yield, and thus, commercial practicality is high.

Accordingly, the N-heterocyclic carbene compound according to the present invention allows numerous derivatives and the transition metal compound based thereon to be synthesized in a very economical manner, and also, it is expected that applications in various fields using the electrochemical properties thereof may be extended.

As described above, though the exemplary embodiments of the present invention have been described in detail, a person with ordinary skill in the art to which the present invention pertains may make various variations of the present invention without departing from the spirit and the scope of the present invention, as defined in the claims which follow. Accordingly, any modification of the following Examples of the present invention may not depart from the technique of the present invention.

What is claimed is:

1. A transition metal compound represented by the following Chemical Formula 1:

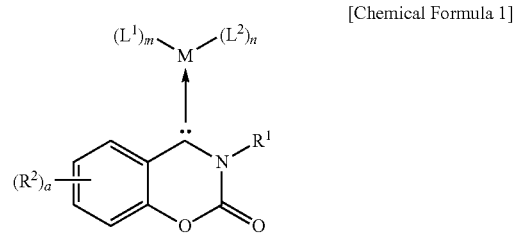

[Chemical Formula 1]

wherein

M is a transition metal;

m is an integer of 1 or 2, n is an integer of 0 to 2, and m+n+1 is an oxidation number of a used transition metal;

$L^1$ is a halogen;

$L^2$ is carbonyl, nitrile, butadiene, pentadiene, hexadiene, cyclooctadiene, allyl, cyclohexene, cyclooctene, or norbornadiene;

a is an integer of 0 to 4;

$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocyclic group, $C_6$-$C_{30}$ aryl, and $C_6$-$C_{30}$ heteroaryl;

$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocyclic group, $C_6$-$C_{30}$ aryl, and $C_6$-$C_{30}$ heteroaryl, and when a is an integer of 2 or more, $R^1$ is the same or different; and alkyl, alkenyl, alkynyl, cycloalkyl, heterocyclic group, aryl, or heteroaryl of $R^1$ and alkyl, alkenyl, alkynyl, alkoxy, alkenyloxy, alkynyloxy, alkylamino, cycloalkyl, heterocyclic group, aryl, or heteroaryl of $R^2$ are independently of one another further substituted by one or more substituents selected from the group consisting of halogen, hydroxy, cyano, $C_1$-$C_{30}$ alkyl, and haloC$_1$-

$C_{30}$ alkyl, and the heterocyclic group of $R^1$ or $R^2$ is of monocyclic or polycyclic non-aromatic ring, and the heteroaryl of $R^1$ or $R^2$ is of monocyclic or polycyclic aromatic, wherein the heterocyclic group or the heteroaryl of $R^1$ or $R^2$ independently comprises 1 to 9 hetero atoms selected from the group consisting of B, N, O, S, Se, Si and P.

2. The transition metal compound of claim 1, wherein M is a transition metal of Groups 6 to 11.

3. The transition metal compound of claim 2, wherein M is a transition metal having an oxidation number of +2 to +4.

4. The transition metal compound of claim 1, wherein a is an integer of 0 to 2;

$R^1$ is $C_1$-$C_{30}$ alkyl, $C_3$-$C_{30}$ cycloalkyl, or $C_1$-$C_{30}$ alkyl $C_6$-$C_{30}$ aryl; and $R^2$ is $C_1$-$C_{30}$ alkoxy, $C_1$-$C_{30}$ alkylamino, halogen, or nitro.

5. The transition metal compound of claim 1, wherein the transition metal compound is selected from the following structures:

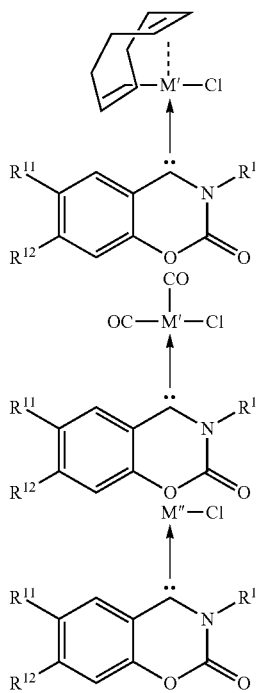

wherein

M' is a Group 9 transition metal;

M" is a Group 11 transition metal;

$R^{11}$ and $R^{12}$ are independently of each other hydrogen, $C_1$-$C_7$ alkoxy, $C_1$-$C_7$ alkylamino, halogen, or nitro; and $R^1$ is $C_1$-$C_7$ alkyl, $C_3$-$C_{12}$ cycloalkyl, or $C_1$-$C_7$ alkyl $C_6$-$C_{12}$ aryl.

6. A preparation method of a transition metal compound represented by the following Chemical Formula 1, the preparation method comprising a process of reacting a compound of the following Chemical Formula A with a carbonate precursor to prepare a compound of the following Chemical Formula B, and reacting a transition metal precursor in the presence of an organic base:

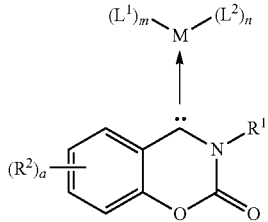

[Chemical Formula 1]

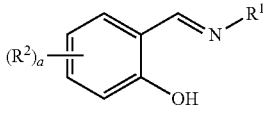

[Chemical Formula A]

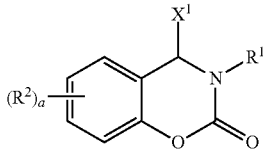

[Chemical Formula B]

wherein

M is a transition metal;

m is an integer of 1 or 2, n is an integer of 0 to 2, and m+n+1 is an oxidation number of a used transition metal;

$L^1$ is a halogen;

$L^2$ is carbonyl, nitrile, butadiene, pentadiene, hexadiene, cyclooctadiene, allyl, cyclohexene, cyclooctene, or norbornadiene;

$X^1$ is a halogen;

a is an integer of 0 to 4;

$R^1$ is selected from the group consisting of $C_1$-$C_{30}$ alkyl, $C_2$-$C_{30}$ alkenyl, $C_2$-$C_{30}$ alkynyl, $C_3$-$C_{30}$ cycloalkyl, $C_3$-$C_{30}$ heterocyclic group, $C_6$-$C_{30}$ aryl, and $C_6$-$C_{30}$ heteroaryl;

$R^2$ is selected from the group consisting of $C_1$-$C_{30}$ alkyl, $C_2$-$C_{30}$ alkenyl, $C_2$-$C_{30}$ alkynyl, $C_1$-$C_{30}$ alkoxy, $C_2$-$C_{30}$ alkenyloxy, $C_2$-$C_{30}$ alkynyloxy, $C_1$-$C_{30}$ alkylamino, halogen, nitro, $C_3$-$C_{30}$ cycloalkyl, $C_3$-$C_{30}$ heterocyclic group, $C_6$-$C_{30}$ aryl, and $C_6$-$C_{30}$ heteroaryl, and when a is an integer of 2 or more, $R^1$ is the same or different; and alkyl, alkenyl, alkynyl, cycloalkyl, heterocyclic group, aryl, or heteroaryl of $R^1$ and alkyl, alkenyl, alkynyl, alkoxy, alkenyloxy, alkynyloxy, alkylamino, cycloalkyl, heterocyclic group, aryl, or heteroaryl of $R^2$ are independently of one another further substituted by one or more substituents selected from the group consisting of halogen, hydroxy, cyano, $C_1$-$C_{30}$ alkyl, and halo$C_1$-$C_{30}$ alkyl, and the heterocyclic group of $R^1$ or $R^2$ is of monocyclic or polycyclic non-aromatic ring, and the heteroaryl of R1 or R2 is of monocyclic or polycyclic aromatic, wherein the heterocyclic group or the heteroaryl of R1 or R2 independently comprises 1 to 9 hetero atoms selected from the group consisting of B, N, O, S, Se, Si and P.

7. The preparation method of claim 6, wherein the carbonate precursor is selected from the group consisting of phosgene, diphosgene, triphosgene, and bromophosgene.

8. The preparation method of claim 6, wherein the organic base is selected from the group consisting of lithium hexamethyldisilazide, sodium hexamethyldisilazide, potassium hexamethyldisilazne, and lithium diisopropylamide.

9. The preparation method of claim 6, wherein the transition metal precursor is selected from the group consisting of $Na_2PdCl_4$, $PdCl_2$, $Pd(OAc)_2$, $RhCl_3$, $[Rh(COD)Cl]_2$, $IrCl_3$, $[Ir(COD)Cl]_2$, $Na_2PtCl_4$, $PtCl_2$, and $AuCl_3$.

10. The preparation method of claim 6, further comprising injecting carbon monoxide into a reaction solution, after the process.

* * * * *